(12) United States Patent
Takaki et al.

(10) Patent No.: US 8,715,730 B2
(45) Date of Patent: May 6, 2014

(54) THERAPEUTIC OR PROPHYLACTIC AGENT FOR DYSKINESIA

(75) Inventors: Suguru Takaki, Kamakura (JP); Kotoe Ohta, Kamakura (JP); Yasuhide Horiuch, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 117 days.

(21) Appl. No.: 13/257,820

(22) PCT Filed: Mar. 29, 2010

(86) PCT No.: PCT/JP2010/055517
§ 371 (c)(1),
(2), (4) Date: Nov. 22, 2011

(87) PCT Pub. No.: WO2010/113841
PCT Pub. Date: Oct. 7, 2010

(65) Prior Publication Data
US 2012/0058186 A1  Mar. 8, 2012

(30) Foreign Application Priority Data
Mar. 30, 2009 (JP) .................................. 2009-081916

(51) Int. Cl.
*A61K 9/32* (2006.01)

(52) U.S. Cl.
USPC ....................................................... 424/482

(58) Field of Classification Search
USPC ....................................................... 424/482
See application file for complete search history.

(56) References Cited

U.S. PATENT DOCUMENTS

| 6,207,199 | B1 | 3/2001 | Allen et al. |
| 2002/0103285 | A1 | 8/2002 | Jordan et al. |
| 2003/0023617 | A1 | 1/2003 | Hunt et al. |
| 2003/0099690 | A1 | 5/2003 | Awamura et al. |
| 2005/0142199 | A1 | 6/2005 | Tian et al. |
| 2008/0274178 | A1* | 11/2008 | Imamoto et al. ............. 424/465 |

FOREIGN PATENT DOCUMENTS

| JP | 54-28812 | | 3/1979 |
| JP | 8-59512 | A | 3/1996 |
| JP | 9-511489 | A | 11/1997 |
| JP | 11-116469 | A | 4/1999 |
| JP | 2000-169365 | A | 6/2000 |
| JP | 2003-509339 | A | 3/2003 |
| JP | 2005-519924 | A | 7/2005 |
| JP | 2005-524654 | A | 8/2005 |
| JP | 2007-91620 | A | 4/2007 |
| JP | 2008-261849 | A | 10/2008 |
| WO | WO 99/02158 | A1 | 1/1999 |
| WO | WO 2008/133330 | A1 | 11/2008 |

OTHER PUBLICATIONS

International Search Report, PCT/JP2010/055517, Apr. 27, 2010.

* cited by examiner

*Primary Examiner* — Adam C Milligan
(74) *Attorney, Agent, or Firm* — Birch, Stewart, Kolasch & Birch, LLP.

(57) ABSTRACT

The present invention relates to a stable orally disintegrating coated tablet containing a drug, wherein the tablet is coated with a coating layer containing a water-soluble substance and a polyvinyl alcohol resin of not less than 5% by weight based on the weight of the coating layer, the water-soluble substance dissolving in an amount of 1 g or more in less than 10 mL of water at 20° C., having a hydroxyl group(s) in its molecule, and having a molecular weight of not more than 200 per a unit hydroxyl group. There is provided a stable orally disintegrating coated tablet which does not cause a crack in the coating layer even when the orally disintegrating tablet has been swollen by moisture absorption under high humidity, while ensuring rapid disintegration properties in an oral cavity. In the case of an orally disintegrating tablet containing a light-unstable drug, degradation of the drug can be suppressed by blending a light shading agent in the coating layer.

5 Claims, No Drawings

THERAPEUTIC OR PROPHYLACTIC AGENT FOR DYSKINESIA

TECHNICAL FIELD

The present invention relates to a stable orally disintegrating coated tablet. More particularly, the present invention relates to a stable orally disintegrating coated tablet containing a drug, wherein the tablet is coated with a coating layer containing a water-soluble substance and a polyvinyl alcohol resin of not less than 5% by weight based on the weight of the coating layer, the water-soluble substance dissolving in an amount of 1 g or more in less than 10 mL of water at 20° C., having a hydroxyl group(s) in its molecule, and having a molecular weight of not more than 200 per a unit hydroxyl group.

BACKGROUND ART

Tablet coating, which is a treatment for forming a thin film-like substance on a tablet surface, is carried out for the purpose of imparting various functions, depending on the composition to be coated, such as improved appearance, water resistance, improved friability, light stability, and distinguishability.

Orally disintegrating tablets which rapidly disintegrate in an oral cavity have now been developed as an easy-to-take formulation for patients with impaired swallowing function due to various causes such as diseases, aging, and decreased saliva production. The orally disintegrating tablets are special formulations which, in view of easiness for patients to take, are required to have an overwhelmingly high disintegration rate compared to that of general tablets and pursue high disintegration rate. However, rapid disintegration properties and high tablet hardness are generally contradictory properties, and therefore orally disintegrating tablets cause chips and cracks of the tablets when divided because of their insufficient tablet hardness and high friability, and it has been pointed out that the orally disintegrating tablets have a problem in handling at dispensing sites. Further, tablets are subject to influence of storage environments such as light, temperature, and humidity because they are stored in the unpacked form in a divider before being automatically divided and are stored in the simply packed form after being divided, and there has been a disadvantage that drugs sensitive to these external environments are inapplicable. In this regard, for example, in cases where a light-unstable drug is tableted, the tablet is generally stabilized by being coated with a coating layer to which a light shading agent is added, but in the case of the orally disintegrating tablets, there is a concern that disintegration is delayed by the coating layer, and stabilization by light shading coating on the tablet itself is difficult.

In addition, many of the orally disintegrating tablets cause a volume expansion under high humidity because the orally disintegrating tablets are provided with rapid disintegration properties by the addition of a hygroscopic excipient and a powerful disintegrator. Therefore, in order for an orally disintegrating tablet to be a coated tablet, it requires not only rapid disintegration properties but also extensibility of the coating layer, but at present there are no conventionally known coated compositions which have an ability to withstand the expansion of a tablet while maintaining orally disintegrating properties.

On the other hand, it is conventionally known that polyvinyl alcohol is used as a coating polymer in the general tablets. There are disclosures of preventing crack occurrence in a coating layer during storage by coating an expansible tablet with polyvinyl alcohol (for example, Patent Document 1). There are also disclosures of preventing crack occurrence in a coating layer during storage by coating an expansible tablet with polyvinyl alcohol with saccharides and a viscosity reducer being added (for example, Patent Document 2). Further, there are disclosures of reducing cracks of the tablet by providing a coating layer of water-soluble polymer and saccharides as an intermediate layer of a sugar-coated tablet (for example, Patent Document 3). However, all these reports only disclose that polyvinyl alcohol films exhibit excellent extension and do not disclose that when polyvinyl alcohol is coated on an orally disintegrating tablet, the tablet exhibits such an excellent rapid solubility that allows easy taking in an oral cavity.

On the other hand, another example of the easy-to-take formulation for the above-described purpose is an orally disintegrating film preparation which disintegrates in an oral cavity. As the film preparation, compositions obtained by adding saccharides to water-soluble polymer such as hydroxypropylmethylcellulose are disclosed (for example, Patent Document 4), but these disclosures mainly focus on disintegration properties and do not describe film extension. Rather, film extension in the film preparation, for example, causes undesirable forms such as a softened film, and is essentially different from the requirements for the coating layer of an orally disintegrating tablet.

Further, there are disclosures of methods of forming a coating layer by melting soluble powder such as low melting point polymer in order to improve the insufficient tablet hardness and high friability of an orally disintegrating tablet (for example, Patent Document 5). However, melting technique, by which it is difficult to form a coating layer uniformly on the whole tablet, is inadequate as a light stabilization method. As a dosing preparation for a drug absorbed via oral mucosa, preparations obtained by coating an orally disintegratable core with a composition composed of gellan gum are disclosed (for example, Patent Document 6). However, the extension of the coating layer is not reported at all.

On the other hand, as a method of stabilizing nalfurafine hydrochloride, there are disclosures of solid preparations containing sodium thiosulfate, saccharides or sugar alcohols, and low-substituted hydroxypropylcellulose, the disclosures also describing that the preparations are coated tablets (for example, Patent Document 7 and Patent Document 8). However, they only disclose that general coated compositions can be coated and do not describe at all the excellent rapid disintegration properties necessary for orally disintegrating tablets or the effect of preventing cracks in a coating layer during storage, and therefore the present invention cannot easily be inferred from these reports.

PRIOR ART DOCUMENTS

Patent Documents

[Patent Document 1] JP 2007-091620 A
[Patent Document 2] JP 54-28812 A
[Patent Document 3] JP 2000-169365 A
[Patent Document 4] JP 11-116469 A
[Patent Document 5] JP 2005-524654 W
[Patent Document 6] JP 2005-519924 W
[Patent Document 7] WO 2008/133330
[Patent Document 8] WO 99/02158

SUMMARY OF THE INVENTION

Problems to be Solved by the Invention

It is an object of the present invention to provide a stable orally disintegrating coated tablet which does not cause a crack in the coating layer even when the orally disintegrating tablet has been swollen by moisture absorption under high humidity, while ensuring rapid disintegration properties in an oral cavity. It is also an object of the present invention, in the case of an orally disintegrating tablet containing a light-unstable drug, to suppress the degradation of the drug by blending a light shading agent in the coating layer.

Means for Solving the Problems

Tablet coating is carried out for the purpose of, for example, improving appearance, imparting water resistance, improving friability, light stabilization, and imparting distinguishability. However, orally disintegrating tablets are generally expanded by moisture absorption particularly under high humidity by their nature to have rapid disintegration properties, and therefore it became clear that cracks occur in the coating layer during storage when coating polymer such as widely-used hydroxypropylmethylcellulose is used. It also became clear that by coating the tablets, disintegration of the coating layer becomes rate-limiting, making it difficult to maintain the rapid disintegration properties.

Thus, the present inventors intensively studied in order to develop a stable orally disintegrating coated tablet which has rapid disintegration properties and further does not cause a crack even under high humidity, and consequently discovered that a stable orally disintegrating coated tablet which has excellent rapid disintegration properties and further does not cause a crack even under high humidity can be obtained only when using the combination of polyvinyl alcohol resin, among polymers used for coating the tablet, and a water-soluble substance dissolving in an amount of 1 g or more in less than 10 mL of water at 20° C., having a hydroxyl group(s) in its molecule, and having a molecular weight of not more than 200 per a unit hydroxyl group (hereinafter, also referred to as the water-soluble substance of the present invention for short). The present inventors also discovered that in the case of the tablet containing a light-unstable drug, degradation of the drug is suppressed by blending a light shading agent in the coating layer, thereby completing the present invention.

Thus, the present invention relates to the invention as described below.

[1] A stable orally disintegrating coated tablet containing a drug, wherein the tablet is coated with a coating layer containing a water-soluble substance and a polyvinyl alcohol resin of not less than 5% by weight based on the weight of the coating layer, the water-soluble substance dissolving in an amount of 1 g or more in less than 10 mL of water at 20° C., having a hydroxyl group(s) in its molecule, and having a molecular weight of not more than 200 per a unit hydroxyl group.
[2] The stable orally disintegrating coated tablet according to [1], wherein said water-soluble substance is at least one of saccharides, sugar alcohols, and polyhydric alcohols.
[3] The stable orally disintegrating coated tablet according to [1], wherein said water-soluble substance is at least one of maltose, maltitol, sorbitol, xylitol, glycerin, fructose, glucose, lactitol, isomaltose, lactose, erythritol, mannitol, trehalose, sucrose, and polyethylene glycol having an average molecular weight of not more than 400.
[4] The stable orally disintegrating coated tablet according to [1], wherein the polyvinyl alcohol resin in the coating layer has a content of 10 to 60% by weight based on the weight of the coating layer.
[5] The stable orally disintegrating coated tablet according to [1], characterized in that weight ratio of the polyvinyl alcohol resin in the coating layer to said water-soluble substance is 1:0.1 to 1:9.
[6] The stable orally disintegrating coated tablet according to [1], characterized in that the coating layer disintegrates in an oral cavity within 18 seconds and the orally disintegrating coated tablet disintegrates in an oral cavity within 60 seconds.
[7] The stable orally disintegrating coated tablet according to [1], characterized in that the coating layer contains a light shading agent.
[8] The stable orally disintegrating coated tablet according to [7], wherein the light shading agent is at least one of titanium oxide, red ferric oxide, yellow ferric oxide, black iron oxide, talc, and kaolin.
[9] The stable orally disintegrating coated tablet according to [7], characterized in that the light shading agent in the coating layer has a content of 0.1 to 40% by weight based on the weight of the coating layer.
[10] The stable orally disintegrating coated tablet according to [1], wherein the drug is at least one of nalfurafine, amlodipine, donepezil, ebastine, selegiline, famotidine, irsogladine, brotizolam, olanzapine, lansoprazole, bepotastine, ramosetron, tamsulosin, naftopidil, polaprezinc, voglibose, rizatriptan, midodrine, risperidone, ondansetron, loratadine, montelukast, azulene sulfonate, etizolam, enalapril, captopril, glibenclamide, chlormadinone acetate, doxazosin, triazolam, domperidone, ketotifen, bromperidol, pravastatin, simvastatin, loperamide, lisinopril, rilmazafone, precipitated calcium carbonate, magnesium oxide, mecobalamin, alfacalcidol, bromocriptine, and pramipexole, and pharmaceutically acceptable salts and solvates thereof.

Effects of the Invention

The present invention provides an orally disintegrating coated tablet of which insufficient tablet hardness, high friability, or degradation by external environmental factors such as light are improved. More particularly, the present invention provides a stable orally disintegrating coated tablet which does not cause a crack in the coating layer even when the orally disintegrating tablet has been swollen by moisture absorption under high humidity, while ensuring rapid disintegration properties in an oral cavity. In the case of an orally disintegrating tablet containing a light-unstable drug, degradation of the drug can be suppressed by blending a light shading agent in the coating layer. These effects allow single-dose packaging of the orally disintegrating tablet which hitherto could not be packaged in a single-dose pack, which in turn improves drug compliance of patients and enhances therapeutic effects.

BEST MODE FOR CARRYING OUT THE INVENTION

The orally disintegrating coated tablet of the present invention will now be described.

Polyvinyl alcohol resin used in the present invention refers to polyvinyl alcohol (PVA) and derivatives or copolymers thereof, and may be generally commercially available one. Specific examples of commercial products of polyvinyl alcohol include, for example, Gohsenol (registered trademark) EG05, EG25, EG30, and EG40 produced by Nippon Synthetic Chemical Industry Co., Ltd.; polyvinyl alcohols 4-88, 5-88, 8-88, 26-88, and 40-88 produced by Merck; and PVA-102, 103, 105, 110, 117, 120, 124, HC, 203, 205, 210, 217, 220, 224, 235, L-8, L-9, L-9-78, L-10, and PVA-505 produced by Kuraray Co., Ltd. Specific examples of commercial products of the copolymers of polyvinyl alcohol include, for example, polyvinyl alcohol-polyethylene glycol graft copolymer, Kollicoat (registered trademark) IR, produced by BASF. Specific examples of commercial products of the derivatives of polyvinyl alcohol include, for example, polyvinyl alcohol copolymers, POVACOAT (registered trademark) Type F, Type R, and Type L produced by Daido Chemical Corporation. A polymer obtained by introducing a polyhydric alcohol group(s) such as glycerin into the side chain of polyvinyl alcohol to reduce the intramolecular interaction of the polyvinyl alcohol, so as to improve a property such as solubility or extensibility of the film formed using the polymer, may also be used. One or more of these specific examples may be used in combination.

The water-soluble substance of the present invention dissolving in an amount of 1 g or more in less than 10 mL of water at 20° C. refers to a water-soluble substance which exhibits, when shaken vigorously for 30 seconds at five-minute intervals at 20±5° C. in accordance with the description about solubility in the Japanese Pharmacopoeia 15th Edition, General Notices, page A-13, such rapid solubility that less than 10 mL of water is sufficient to dissolve 1 g of the substance within 30 minutes. Table 1 shows the list of the terms representing solubility described in the Japanese Pharmacopoeia 15th Edition, General Notices, page A-13. The substances classified as "Very soluble" or "Freely soluble" in Table 1 are suitably used.

TABLE 1

| Terms | Solvent amount required to dissolve 1 g or 1 mL of solute |
|---|---|
| Very soluble | Less than 1 mL |
| Freely soluble | Not less than 1 mL and less than 10 mL |
| Soluble | Not less than 10 mL and less than 30 mL |
| Sparingly soluble | Not less than 30 mL and less than 100 mL |
| Slightly soluble | Not less than 100 mL and less than 1000 mL |
| Very slightly soluble | Not less than 1000 mL and less than 10000 mL |
| Practically insoluble | Not less than 10000 mL |

The water-soluble substance which has a hydroxyl group(s) in its molecule and has a molecular weight of not more than 200 per a unit hydroxyl group means that the value obtained by dividing the molecular weight by the number of a hydroxyl groups in the molecule is not more than 200. When the value is more than 200, sufficient interactions with a polyvinyl alcohol resin cannot be expected, so that extensibility cannot be imparted to a coating layer.

As the water-soluble substance of the present invention, saccharides, sugar alcohols, and polyhydric alcohols are preferred. Examples of these include, for example, maltose, maltitol, sorbitol, xylitol, glycerin, fructose, glucose, lactitol, isomaltose, lactose, erythritol, mannitol, trehalose, sucrose, and polyethylene glycol having an average molecular weight of not more than 400. In view of low hygroscopicity, maltose, maltitol, lactitol, lactose, erythritol, mannitol, trehalose, and isomaltose are preferred; lactose, mannitol, maltitol, and lactitol are more preferred. One or more of these specific examples may be used in combination.

The content of polyvinyl alcohol resin in the coating layer of the present invention can be not less than 5% by weight, preferably 10 to 60% by weight, and more preferably 10 to 40% by weight, based on the weight of the coating layer. When the content of polyvinyl alcohol resin is less than 5% by weight based on the weight of the coating layer, the film formability of polyvinyl alcohol is lost, resulting in that tablets adhere to each other during production and cracks occur in the coating layer under high humidity.

The weight ratio of polyvinyl alcohol resin to the water-soluble substance of the present invention in the coating layer of the present invention is not particularly restricted, but in view of disintegration properties and film formability of polyvinyl alcohol resin, it is preferably 1:0.1 to 1:9, more preferably 1:0.2 to 1:6, and still more preferably 1:0.4 to 1:4.

The stable orally disintegrating coated tablet of the present invention means that cracks are unlikely to occur in the coating layer even when the orally disintegrating tablet has been swollen by moisture absorption under high humidity. Unlikelihood of cracks occurring in the coating layer can be evaluated by allowing the orally disintegrating coated tablet to stand at 40° C. under 75% RH (Relative Humidity) atmosphere for 24 hours and checking the appearance of the coating layer. The extension rate of such coating layer can be 1% or more, preferably 2% or more, and more preferably 4% or more. The extension rate of the coating layer can be determined by measuring a film of 10 mm in width and about 0.075 mm in thickness with a tensile tester (Tensilon) at 25° C. under 60% RH atmosphere at a tensile speed of 100 mm/min, the film being obtained by casting a solution or suspension having a solid content of the coated composition of about 30% by weight on a glass surface using an applicator (YBA type Baker applicator, 0 to 1 mm) at 0.5 mm and drying.

The coating layer of the present invention can optionally contain a light shading agent besides the above-mentioned components. Examples of the light shading agent include, for example, titanium oxide, red ferric oxide, yellow ferric oxide, black iron oxide, talc, and kaolin; preferably, the addition of titanium oxide, red ferric oxide, and yellow ferric oxide produces a sufficient light shading effect. One or more of these specific examples may be used in combination. These light shading agents, when blended in large amounts, cause the loss of film extensibility, and when blended in too small amounts, do not produce a sufficient addition effect; therefore the content of the light shading agent can be 0.1 to 40% by weight, preferably 1 to 35% by weight, and more preferably 5 to 30% by weight, based on the weight of the coating layer.

Besides the above-mentioned components, pharmaceutically acceptable additives can optionally be added to the coating layer of the present invention as long as the effects of the present invention are not impaired. Examples of such additives include, for example, excipients, disintegrators, binders, corrigents, flavoring agents, coloring agents, or lubricants. Examples of excipients include, for example, starches such as corn starch and potato starch, microcrystalline cellulose, and light anhydrous silicic acid. Examples of disintegrators include, for example, partially pregelatinized starch, carmellose calcium, crospovidone, low-substituted hydroxypropylcellulose, croscarmellose sodium, and sodium carboxymethyl starch. Examples of binders include, for example, polyvinyl pyrrolidone, hydroxypropylmethylcellulose, hydroxypropylcellulose, powdered acacia, gelatin, pullulan, carmellose sodium, ethyl cellulose, and aminoalkyl methacrylate copolymer. Examples of corrigents include, for example, aspartame, sucralose, sodium saccharin, glycyrrhizin dipotassium, stevia, thaumatin, and citric acid. Examples of flavoring agents include, for example, menthol, peppermint, lemon, lemon-lime, orange, peppermint oil, and various flavors. Examples of coloring agents include, for example, tar dye, turmeric extract, caramel, carotene solution, beta-carotene, copper chlorophyll, and riboflavin. Examples of lubricants include, for example, surfactants such as polyethylene glycol, liquid paraffin, silicone, and long-chain fatty acid ester, and waxes such as beeswax, carnauba wax, and paraffin. These additives are only illustrative and not restrictive at all. Such additives can be added to the inner and outer surface of the coating layer of the present invention.

In a coating operation of the stable orally disintegrating coated tablet of the present invention, dry coating methods or wet coating methods can be used. Examples of dry coating methods include, for example, the method of coating using a coating layer as an intermediate when tableting, as described in JP 2005-529645 W. Examples of wet coating methods include the method of coating by spraying a coating solution onto the tablet surface and drying. The coating solution is prepared by dissolving or suspending a coating layer composition which contains the water-soluble substance of the present invention and a polyvinyl alcohol resin of not less than 5% by weight based on the weight of the coating layer in water or solvents such as ethanol and methanol. These solvents can be used alone or in combination. In the process of coating the surface of the orally disintegrating tablet, commonly-used apparatuses are used; for example, a pan coating apparatus can be used. Although the operating conditions are not restricted, in the case of an orally disintegrating tablet with high friability, a coating layer can be formed uniformly even at the edge of the tablet by setting the pan rotation at below normal speed. Depending on the shape and size of the preparations, the thickness of the coating layer to be formed, in view of rapid disintegration properties, can be 200 μm or less, preferably 100 μm or less, and more preferably 50 μm or less.

For the oral disintegration time of an orally disintegrating tablet, objective values can be obtained by measuring the time until the tablet has been completely disintegrated by saliva without water or being chewed in the oral cavity of a healthy adult male(s) and female(s) and averaging the measurements of three or more subjects. "Tablet has been completely disintegrated" means the point when the subjects no longer feel a foreign body sensation in the oral cavity. Orally disintegrating tablets are generally designed to disintegrate within 60 seconds without water in an oral cavity, as described in Patricia Van Arnum, "Advancing ODT Technology," Pharmaceutical Technology, Vol. 3, No. 10, pp. 66-76, 2007 (published on Oct. 2, 2007). Therefore, the oral disintegration time of an orally disintegrating coated tablet can be less than 60 seconds, preferably less than 50 seconds, and more preferably less than 40 seconds.

The oral disintegration time of a coating layer can be determined by firstly measuring the oral disintegration time of an orally disintegrating coated tablet, separately measuring the oral disintegration time of the inner core portion obtained by cutting the coating layer of the orally disintegrating coated tablet, and then subtracting the disintegration time of the inner core portion from the disintegration time of the orally disintegrating coated tablet. Since the oral disintegration time of commercially available orally disintegrating tablets is about from 10 seconds to 42 seconds, as described in Okimoto, "The Pharmaceutical Monthly", Jiho Inc., Vol. 50 No. 11, pp. 47-55 (published on Oct. 1, 2008), in order for the oral disintegration time of an orally disintegrating coated tablet to be less than 60 seconds, the oral disintegration time of a coating layer can be less than 18 seconds, preferably less than 15 seconds, and more preferably less than 12 seconds. The orally disintegrating coated tablet of the present invention is not limited to being taken without water, and may be taken with water.

The inner core in the present invention, that is, the orally disintegrating tablet is not particularly restricted with regard to its preparation method and composition as long as the disintegration time in an oral cavity is about 1 to 42 seconds. For example, those which are prepared by conventional methods in the art of preparation such as direct tableting method, indirect tableting method, and molding method can be used. Examples of such preparation methods include, for example, the preparation method of obtaining porous tablets by tableting wet particles, the preparation method utilizing physicochemical properties such as crystallization of saccharides, the preparation method using a lyophilization technique, the preparation method utilizing a disintegrator such as crospovidone, and the preparation method using an external lubricant method.

The drug of the stable orally disintegrating coated tablet in the present invention is not particularly limited, and not restricted as long as it is a drug having pharmacological activity. For example, the drug can contain as a drug at least one of nalfurafine, amlodipine, donepezil, ebastine, selegiline, famotidine, irsogladine, brotizolam, olanzapine, lansoprazole, bepotastine, ramosetron, tamsulosin, naftopidil, polaprezinc, voglibose, rizatriptan, midodrine, risperidone, ondansetron, loratadine, montelukast, azulene sulfonate, etizolam, enalapril, captopril, glibenclamide, chlormadinone acetate, doxazosin, triazolam, domperidone, ketotifen, bromperidol, pravastatin, simvastatin, loperamide, lisinopril, rilmazafone, precipitated calcium carbonate, magnesium oxide, mecobalamin, alfacalcidol, bromocriptine, and pramipexole, and pharmaceutically acceptable salts and solvates thereof. Among them, when at least one of nalfurafine, amlodipine, ebastine, selegiline, brotizolam, ramosetron, midodrine, montelukast, azulene sulfonate, etizolam, bromperidol, mecobalamin, alfacalcidol, bromocriptine, and pramipexole, and pharmaceutically acceptable salts and solvates thereof is contained as a drug, it is preferable to add a light shading agent to the present coating layer because they are unstable to light.

An example of the method of producing an orally disintegrating tablet containing nalfurafine or a pharmaceutically acceptable salt and/or solvate thereof is that an orally disintegrating tablet can be prepared by granulating powder mannitol (such as PEARLITOL (registered trademark) 50C produced by Roquette Japan K.K.) and crospovidone (such as Kollidon CL produced by BASF), mixing the resulting granules with the other granulated granules obtained by granulating granular mannitol (such as PEARLITOL (registered trademark) 300DC produced by Roquette Japan K.K.) and nalfurafine or a pharmaceutically acceptable salt and/or solvate thereof, and tableting the resulting mixture. By setting the blending ratio of powder mannitol to granular mannitol at about 1:9 to 1:1 in weight ratio, the orally disintegrating tablet can have excellent tabletability and disintegration properties. In addition, a stabilizing agent can be blended for ensuring the stability of nalfurafine or a pharmaceutically acceptable salt and/or solvate thereof in the preparation; for example, sodium thiosulfate can be blended. The granulated granules of nalfurafine or a pharmaceutically acceptable salt and/or solvate thereof and granulated mannitol can be produced by the wet granulation method comprising the steps of dissolving or suspending, for example, nalfurafine or a pharmaceutically acceptable salt and/or solvate thereof and sodium thiosulfate together in water or a pharmaceutically acceptable solvent and adding the resultant to granulated mannitol. In the wet granulation, commonly-used apparatuses are used; for example, a fluidized bed granulator, tumbling fluidized bed granulator, stirring granulator, cylindrical extrusion granulator, and wet extrusion granulator can be used. In the step of tableting, commonly-used apparatuses are used; for example, a single punch tableting machine and rotary tableting machine can be used. The molding pressure in tableting may be set such that the tablet has enough hardness that does not pose a problem in coating operation. Although the shape of the tablet is also not particularly restricted, a WR tablet tends to have improved friability.

EXAMPLES

The present invention will now be described by way of examples to clarify its excellent effects, but the present invention is not restricted thereto.

Reference Example 1

Mannitol (PEARLITOL 300DC, Roquette Japan K.K.) was weighed in an amount of 96.745 parts by weight (hereinafter, abbreviated as "parts" and the same shall apply hereinafter unless otherwise noted.), sieved through Mesh with 1 mm openings, and loaded into a fluidized bed granulator (FLO-5, Freund Industrial Co., Ltd.). Next, onto these granules, the spray solution obtained by dissolving 0.005 parts of nalfurafine hydrochloride and 0.1 parts of sodium thiosulfate hydrate in distilled water was sprayed to produce granulated granules. Mannitol (PEARLITOL 50C, Roquette Japan K.K.) was then weighed out in an amount of 25.87 parts, sieved through Mesh with 1 mm openings, and loaded into a stirring granulator (NMG-3L, NARA MACHINERY CO., LTD.) together with 6.5 parts of crospovidone (Kollidon CL, BASF). Subsequently, the resultant was granulated while adding thereto distilled water in which 0.13 parts of red ferric oxide (Kishi Kasei) was dispersed to produce granulated material. The granulated granules produced with the fluidized bed granulator and the granulated granules produced with the stirring granulator were treated individually using Comil to obtain sized granules. To 129.35 parts of the sized granules, 0.65 parts of magnesium stearate (Taihei Chemical Industrial Co., Ltd.) was added and mixed for five minutes. The granules obtained were made into WR tablets of 130 mg using a tableting machine (Correct19, KIKUSUI SEISAKUSHO LTD.).

Example 1

Ten parts of PVA (polyvinyl alcohol 4-88, Merck) and 90 parts of maltitol (MALTISOR BP200, Roquette Japan K.K.) were dissolved in distilled water to prepare a coating solution having a solid content of 10% by weight. Into a film coating machine (DRC-200, Powrex Corporation), 200 g of the orally disintegrating tablets prepared in Reference Example 1 was loaded, and the coating solution was sprayed thereonto to provide 131.95 mg of orally disintegrating coated tablets having 1.95 mg of coating layers per 130 mg of tablets.

Example 2

Coating was carried out in the same manner except that an aqueous solution having a solid content of 10% by weight composed of 60 parts of a polyvinyl alcohol resin, POVA-COAT (TYPE F, Daido Chemical Corporation), 5 parts of glycerin (Japanese Pharmacopoeia concentrated glycerin, Asahi Denka Kogyo K.K.), and 35 parts of lactose (Pharmtose 200M, DMV) was used in place of the coating solution in Example 1 to provide 133.9 mg of orally disintegrating coated tablets having 3.9 mg of coating layers per 130 mg of tablets.

Example 3

Coating was carried out in the same manner except that a water dispersion having a solid content of 10% by weight composed of 60 parts of PVA, 6 parts of glycerin, and 34 parts of crospovidone (Kollidon CLSF, BASF) was used in place of the coating solution in Example 1 to provide 133.9 mg of orally disintegrating coated tablets having 3.9 mg of coating layers per 130 mg of tablets.

Comparative Example 1

Coating was carried out in the same manner except that an aqueous solution having a solid content of 10% by weight composed of 60 parts of PVA and 40 parts of PEG6000 (NOF CORPORATION) was used in place of the coating solution in Example 1 to provide 133.9 mg of coated tablets having 3.9 mg of coating layers per 130 mg of tablets.

Comparative Example 2

Coating was carried out in the same manner except that an aqueous solution having a solid content of 10% by weight composed of 60 parts of PVA and 40 parts of sodium lauryl sulfate (Nikko Chemicals Co., Ltd.) was used in place of the coating solution in Example 1 to provide 133.9 mg of coated tablets having 3.9 mg of coating layers per 130 mg of tablets.

Comparative Example 3

Coating was carried out in the same manner except that a water dispersion having a solid content of 10% by weight composed of 60 parts of PVA and 40 parts of low-substituted hydroxypropylcellulose (L-HPC) (LH-31, Shin-Etsu Chemical Co., Ltd.) was used in place of the coating solution in Example 1 to provide 133.9 mg of coated tablets having 3.9 mg of coating layers per 130 mg of tablets.

Comparative Example 4

Coating was carried out in the same manner except that a water dispersion having a solid content of 10% by weight composed of 60 parts of PVA and 40 parts of crystal cellulose (CEOLUS PH-101, Asahi Kasei Chemicals Corporation) was used in place of the coating solution in Example 1 to provide 133.9 mg of coated tablets having 3.9 mg of coating layers per 130 mg of tablets.

Comparative Example 5

Coating was carried out in the same manner except that a water dispersion having a solid content of 10% by weight composed of 60 parts of PVA and 40 parts of talc (Crown talc PP, Matsumura Sangyo Co., Ltd.) was used in place of the coating solution in Example 1 to provide 133.9 mg of coated tablets having 3.9 mg of coating layers per 130 mg of tablets.

Comparative Example 6

Coating was carried out in the same manner except that a water dispersion having a solid content of 10% by weight composed of 60 parts of PVA and 40 parts of crospovidone was used in place of the coating solution in Example 1 to provide 133.9 mg of coated tablets having 3.9 mg of coating layers per 130 mg of tablets.

Comparative Example 7

Coating was carried out in the same manner except that an aqueous solution having a solid content of 10% by weight composed of 3 parts of PVA and 97 parts of maltitol was used in place of the coating solution in Example 1.

Example 4

Coating was carried out in the same manner except that a water dispersion having a solid content of 10% by weight composed of 60 parts of PVA, 2.5 parts of glycerin, and 37.5 parts of low-substituted hydroxypropylcellulose (L-HPC) (LH-31, Shin-Etsu Chemical Co., Ltd.) was used in place of the coating solution in Example 1 to provide 133.9 mg of orally disintegrating coated tablets having 3.9 mg of coating layers per 130 mg of tablets.

Example 5

Coating was carried out in the same manner except that an aqueous solution having a solid content of 10% by weight composed of 70 parts of PVA and 30 parts of maltitol was used in place of the coating solution in Example 1 to provide 133.9 mg of orally disintegrating coated tablets having 3.9 mg of coating layers per 130 mg of tablets.

Example 6

Coating was carried out in the same manner except that a water dispersion having a solid content of 10% by weight composed of 20 parts of PVA, 50 parts of maltitol, 27 parts of titanium oxide (HA-R, Freund Industrial Co., Ltd.), and 3 parts of red ferric oxide was used in place of the coating solution in Example 1 to provide 132.6 mg of orally disintegrating coated tablets having 2.6 mg of coating layers per 130 mg of tablets.

Example 7

Coating was carried out in the same manner except that a water dispersion having a solid content of 10% by weight composed of 30 parts of PVA, 40 parts of maltitol, 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 8

Coating was carried out in the same manner except that a water dispersion having a solid content of 10% by weight composed of 40 parts of PVA, 30 parts of maltitol, 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 9

Coating was carried out in the same manner except that a water dispersion having a solid content of 10% by weight composed of 30 parts of PVA, 38 parts of maltitol, 27 parts of titanium oxide, 3 parts of red ferric oxide, and 2 parts of silicone (SH200C FLUID100CS, Dow Corning Toray) was used in place of the coating solution in Example 1 to provide 133.9 mg of orally disintegrating coated tablets having 3.9 mg of coating layers per 130 mg of tablets.

Example 10

Coating was carried out in the same manner except that a water dispersion having a solid content of 10% by weight composed of 30 parts of PVA, 20 parts of maltitol, 20 parts of lactitol (Lactitol MC, Danisco Japan Ltd.), 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 11

Coating was carried out in the same manner except that a water dispersion having a solid content of 10% by weight composed of 30 parts of PVA, 40 parts of lactitol, 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 12

Coating was carried out in the same manner except that a water dispersion having a solid content of 10% by weight composed of 20 parts of PVA, 45 parts of lactitol, 27 parts of titanium oxide, 3 parts of red ferric oxide, and 5 parts of polishing wax (103, Freund Industrial Co., Ltd.) was used in place of the coating solution in Example 1 to provide 133.9 mg of orally disintegrating coated tablets having 3.9 mg of coating layers per 130 mg of tablets.

Example 13

Coating was carried out in the same manner except that a water dispersion having a solid content of 10% by weight composed of 30 parts of PVA, 40 parts of trehalose (Trehalose G, Asahi Kasei Chemicals Corporation), 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 14

Coating was carried out in the same manner except that a water dispersion having a solid content of 10% by weight composed of 30 parts of PVA, 40 parts of mannitol (PEARLITOL 50C, Roquette Japan K.K.), 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 15

Coating was carried out in the same manner except that a water dispersion having a solid content of 10% by weight composed of 30 parts of PVA, 40 parts of maltose (purified maltose, HAYASHIBARA), 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 16

Coating was carried out in the same manner except that a water dispersion having a solid content of 10% by weight composed of 30 parts of PVA, 40 parts of erythritol (NIKKEN CHEMICAL AND SYNTHETIC INDUSTRY CO., LTD.), 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 17

Coating was carried out in the same manner except that a water dispersion having a solid content of 10% by weight composed of 30 parts of PVA, 35 parts of lactose, 5 parts of glycerin, 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Comparative Example 8

Coating was carried out in the same manner except that a water dispersion having a solid content of 10% by weight composed of 30 parts of hydroxypropylmethylcellulose (HPMC) (TC-5R, Shin-Etsu Chemical Co., Ltd.), 35 parts of lactose, 5 parts of glycerin, 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 18

Coating was carried out in the same manner except that a water dispersion having a solid content of 10% by weight composed of 30 parts of PVA, 5 parts of maltitol, 10 parts of lactitol, 25 parts of lactose, 27 parts of titanium oxide, and 3 parts of red ferric oxide was used in place of the coating solution in Example 1 to provide 133.9 mg of orally disintegrating coated tablets having 3.9 mg of coating layers per 130 mg of tablets.

Example 19

A water dispersion having a solid content of 10% by weight composed of 30 parts of PVA, 5 parts of maltitol, 10 parts of lactitol, 25 parts of lactose, 27 parts of titanium oxide, and 3 parts of red ferric oxide was prepared. Into a film coating machine (DRC-200, Powrex Corporation), 200 g of Amlodin (registered trademark) OD Tablets 2.5 mg (Dainippon Sumitomo Pharma Co., Ltd.) containing amlodipine besylate as a drug were loaded, and the coating solution was sprayed thereonto to provide 86.3 mg of orally disintegrating coated tablets having 1.3 mg of coating layers per 85 mg of tablets.

Comparative Example 9

A solid preparation was prepared by the method described in JP 54-28812 A (Patent Document 2). Lactose (Pharmatose 200M, DMV) in an amount of 47.2 parts, microcrystalline cellulose (CEOLUS PH-101, Asahi Kasei Chemicals Corporation) in an amount of 35.4 parts, and corn starch (W, Nihon Shokuhin Kako Co., Ltd.) in an amount of 35.4 parts were weighed out and loaded into a stirring granulator (NMG-3L, NARA MACHINERY CO., LTD.). The resultant was granulated while adding thereto distilled water in which 1.2 parts of methyl cellulose (SH-15, Shin-Etsu Chemical Co., Ltd.) was dissolved to produce granulated material. The obtained granulated material and Comil (1975, Powrex Corporation) were used to carry out a treatment to obtain sized granules. To 119.2 parts of the sized granules, 0.8 parts of magnesium stearate (Taihei Chemical industrial Co., Ltd.) was added and mixed for five minutes. The granules obtained were made into tablets of 120 mg using a tableting machine (correct19, KIKUSUI SEISAKUSHO LTD.) (inner core).

Next, 200 g of these tablets were loaded into a film coating machine (DRC-200, Powrex Corporation), and a solution in which 45.2 parts of PVA, 5.65 parts of liquid paraffin (KOKUSAN CHEMICAL Co., Ltd.), 45.2 parts of mannitol, 1.69 parts of Span80 (Wako Pure Chemical Industries, Ltd.), and 2.26 parts of Tween80 (KANTO KAGAKU) were dispersed was sprayed thereonto to provide 123 mg of coated tablets having 3 mg of coating layers per 120 mg of tablets.

Reference Example 2

Mannitol (PEARLITOL 300DC) was weighed in an amount of 96.745 parts by weight, sieved through Mesh with 1 mm openings, and loaded into a fluidized bed granulator. Next, onto these granules, the spray solution obtained by dissolving 0.005 parts of nalfurafine hydrochloride and 0.1 parts of sodium thiosulfate hydrate in distilled water was sprayed to produce granulated granules. Mannitol (PEARLITOL 50C) was then weighed out in an amount of 25.9675 parts, sieved through Mesh with 1 mm openings, and loaded into a stirring granulator (NMG-3L) together with 6.5 parts of crospovidone. Subsequently, the resultant was granulated while adding thereto distilled water in which 0.0325 parts of red ferric oxide was dispersed to produce granulated material. The granulated granules produced with the fluidized bed granulator and the granulated granules produced with the stirring granulator were treated individually using Comil to obtain sized granules. To 129.35 parts of the sized granules, 0.65 parts of magnesium stearate (Taihei Chemical Industrial Co., Ltd.) was added and mixed for five minutes. The granules obtained were made into WR tablets of 130 mg using a tableting machine (Correct19, KIKUSUI SEISAKUSHO LTD.).

Example 20

Thirty parts of PVA, 40 parts of lactose, 27 parts of titanium oxide, and 3 parts of red ferric oxide were dispersed in distilled water to prepare a coating solution having a solid content of 10% by weight. Into a film coating machine, 200 g of the orally disintegrating tablets prepared in Reference Example 2 was loaded, and the coating solution was sprayed thereonto to provide 133.9 mg of orally disintegrating coated tablets having 3.9 mg of coating layers per 130 mg of tablets.

Example 21

A coating solution was prepared in the same manner as in Example 20, and the coating solution was sprayed onto 0.1 mg of Harnal (registered trademark) D Tablets (Astellas Phama Inc.) containing tamsulosin hydrochloride as a drug to provide 122.9 mg of orally disintegrating coated tablets having 3.7 mg of coating layers per 119.2 mg of tablets.

Example 22

A coating solution was prepared in the same manner as in Example 20, and the coating solution was sprayed onto 10 mg of Gamofa (registered trademark) D Tablets (Sandoz) containing famotidine as a drug to provide 131.6 mg of orally disintegrating coated tablets having 3.6 mg of coating layers per 128.0 mg of tablets.

Example 23

A coating solution was prepared in the same manner as in Example 20, and the coating solution was sprayed onto 5 mg of Ebastel (registered trademark) OD Tablets (Dainippon Sumitomo Pharma Co., Ltd.) containing ebastine as a drug to provide 103.9 mg of orally disintegrating coated tablets having 2.9 mg of coating layers per 101.0 mg of tablets.

Example 24

A coating solution was prepared in the same manner as in Example 20, and the coating solution was sprayed onto Takepron (registered trademark) OD Tablets 15 (Takeda Pharmaceutical Company Limited) containing lansoprazole as a drug to provide 296.6 mg of orally disintegrating coated tablets having 13.0 mg of coating layers per 283.6 mg of tablets.

Example 25

A coating solution was prepared in the same manner as in Example 20, and the coating solution was sprayed onto 0.2 mg of Voglibose OD Tablets "TOWA" (Towa Pharmaceutical Co., Ltd.) containing voglibose as a drug to provide 137.4 mg of orally disintegrating coated tablets having 1.8 mg of coating layers per 135.6 mg of tablets.

Example 26

A coating solution was prepared in the same manner as in Example 20, and the coating solution was sprayed onto 0.25 mg of Lendormin (registered trademark) D Tablets (Boehringer Ingelheim) containing brotizolam as a drug to provide 172.3 mg of orally disintegrating coated tablets having 4.9 mg of coating layers per 167.4 mg of tablets.

Example 27

1. Measurement of Oral Disintegration Time

For the orally disintegrating coated tablets obtained in Examples 1 to 26, Comparative Examples 1 to 6, Comparative Example 8, and Comparative Example 9, oral disintegration time was measured in three subjects consisting of a healthy adult male(s) and female(s). The time calculated by subtracting the oral disintegration time of the inner core tablet from the oral disintegration time of the orally disintegrating coated tablet was defined as the oral disintegration time of the coating layer (Table 2).

2. Crack in Coating Layer Under High Humidity

For the orally disintegrating coated tablets obtained in Examples 1 to 26, Comparative Examples 1 to 6, Comparative Example 8, and Comparative Example 9, the presence of cracks in the coating layer was evaluated by visually observing the tablet after storing at 40° C. and 75% RH for one day (Table 2).

3. Light Stability Testing

The inner core (Reference Example 1) used in Example 7 and the orally disintegrating coated tablet of Example 7 were spread out on a Petri dish so that they do not overlap, and irradiated with white fluorescent light (2000 Lux/hr, total 600,000 Lux), after which the stability was evaluated by measuring the percentage of residual drug (%) by HPLC method under the following conditions (Table 3).
Column: Inertsil ODS-3 (inner diameter 3.0 mm×length 150 mm, particle size 5 μm)
Guard column: Cartridge column E (inner diameter 3.0 mm×length 10 mm, particle size 5 μm)
Mobile phase: 25 mmol phosphate buffer (pH 4.5)/acetonitrile mixture (77.5:22.5) (v/v)
Flow rate: 0.5 mL/min
Detection wavelength: 280 nm

4. Measurement of Tablet Hardness

The inner core (Reference Example 1) used in Example 7 and the orally disintegrating coated tablet of Example 7 were measured using a hardness tester (TABLET TESTER6D, Schleuniger) (Table 4).

5. Measurement of Friability

Friability of Amlodin (registered trademark) OD Tablets 2.5 mg and the coated tablets of Amlodin (registered trademark) OD Tablets 2.5 mg obtained in Example 19 were measured immediately after production and after storage under the conditions of 40° C. and 75% RH for two hours in accordance with the Friability Test described in the Japanese Pharmacopoeia 15th Edition, General Notices, page F-131 (Table 5).

TABLE 2

Formula, disintegration time, and cracks in coating layer after storage at 40° C. under 75% RH

| | Component | Molecular weight of not more than 200 per a unit hydroxyl group | Water-soluble substance dissolving in an amount of 1 g or more in less than 10 mL of water at 20° C. | Com. Ex. 1 | Com. Ex. 2 | Com. Ex. 3 | Com. Ex. 4 | Com. Ex. 5 | Com. Ex. 6 | Com. Ex. 7 | Com. Ex. 8 | Com. Ex. 9 |
|---|---|---|---|---|---|---|---|---|---|---|---|---|
| Additive | PEG6000 | x | o | 40 | | | | | | | | |
| | Sodium lauryl sulfate | x | o | | 40 | | | | | | | |
| | L-HPC | o | x | | | 40 | | | | | | |
| | Microcrystalline cellulose | o | x | | | | 40 | | | | | |
| | Talc | o | x | | | | | 40 | | | | |
| | Crospovidone | x | x | | | | | | 40 | | | |
| | Maltitol | o | o | | | | | | | | | 97 |

TABLE 2-continued

Formula, disintegration time, and cracks in coating layer after storage at 40° C. under 75% RH

| | Component | | | | | | | | | | | |
|---|---|---|---|---|---|---|---|---|---|---|---|---|
| | Lactose | o | o | | | | | | | | 35 | |
| | Glycerin | o | o | | | | | | | | 5 | |
| | Lactitol | o | o | | | | | | | | | |
| | Trehalose | o | o | | | | | | | | | |
| | Mannitol | o | o | | | | | | | | | 45.2 |
| | Maltose | o | o | | | | | | | | | |
| | Erythritol | | | | | | | | | | | |
| Polymer | PVA | | | 60 | 60 | 60 | 60 | 60 | 60 | 3 | | 45.2 |
| | PVACOAT | | | | | | | | | | | |
| | HPMC | | | | | | | | | | 30 | |
| Lubricant | Silicone | | | | | | | | | | | |
| | Polishing wax | | | | | | | | | | | |
| | Span80 | | | | | | | | | | | 1.69 |
| | Tween80 | | | | | | | | | | | 2.26 |
| | Liquid paraffin | | | | | | | | | | | 5.65 |
| Light shading agent | Titanium oxide | | | | | | | | | | 27 | |
| | Red ferric oxide | | | | | | | | | | 3 | |
| Evaluation | Oral disintegration time of coated tablet (sec) | | | 27 | 31 | 31 | 29 | 30 | 28 | not produced | 21 | 94 |
| | Oral disintegration time of coating layer (sec) | | | 17 | 22 | 22 | 20 | 21 | 19 | not produced | 12 | 14 |
| | Cracks after storage at 40° C. under 75% RH for one day | | | present | absent | absent | absent | absent | absent | not produced | present | absent |
| | The water-soluble substance of the present invention/Polyvinyl alcohol resin | | | — | — | — | — | — | — | 32 | — | 1 |

| | Component | Molecular weight of not more than 200 per a unit hydroxyl group | Water-soluble substance dissolving in an amount of 1 g or more in less than 10 mL of water at 20° C. | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|---|
| Additive | PEG6000 | x | o | | | | | | | | | |
| | Sodium lauryl sulfate | x | o | | | | | | | | | |
| | L-HPC | o | x | | | | | 37.5 | | | | |
| | Microcrystalline cellulose | o | x | | | | | | | | | |
| | Talc | o | x | | | | | | | | | |
| | Crospovidone | x | x | | | | 34 | | | | | |
| | Maltitol | o | o | 90 | | | | | 30 | 50 | 40 | 30 | 38 |
| | Lactose | o | o | | 35 | | | | | | | |
| | Glycerin | o | o | | 5 | 6 | 2.5 | | | | | |
| | Lactitol | o | o | | | | | | | | | |
| | Trehalose | o | o | | | | | | | | | |
| | Mannitol | o | o | | | | | | | | | |
| | Maltose | o | o | | | | | | | | | |
| | Erythritol | | | | | | | | | | | |
| Polymer | PVA | | | 10 | | 60 | 60 | 70 | 20 | 30 | 40 | 30 |
| | PVACOAT | | | | 60 | | | | | | | |
| | HPMC | | | | | | | | | | | |
| Lubricant | Silicone | | | | | | | | | | | 2 |
| | Polishing wax | | | | | | | | | | | |
| | Span80 | | | | | | | | | | | |
| | Tween80 | | | | | | | | | | | |
| | Liquid paraffin | | | | | | | | | | | |
| Light shading agent | Titanium oxide | | | | | | | | 27 | 27 | 27 | 27 |
| | Red ferric oxide | | | | | | | | 3 | 3 | 3 | 3 |
| Evaluation | Oral disintegration time of coated tablet (sec) | | | 11 | 21 | 22 | 26 | 26 | 14 | 18 | 18 | 18 |
| | Oral disintegration time of coating layer (sec) | | | 2 | 12 | 13 | 17 | 17 | 5 | 10 | 9 | 9 |
| | Cracks after storage at 40° C. under 75% RH for one day | | | absent | absent | absent | absent | absent | absent | absent | absent | absent |
| | The water-soluble substance of the present invention/Polyvinyl alcohol resin | | | 9 | 0.66 | 0.1 | 0.04 | 0.43 | 2.5 | 1.33 | 0.75 | 1.27 |

| | Component | Molecular weight of not more than 200 per a unit hydroxyl group | Water-soluble substance dissolving in an amount of 1 g or more in less than 10 mL of water at 20° C. | Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|---|---|---|
| Additive | PEG6000 | x | o | | | | | | | | | |

TABLE 2-continued

Formula, disintegration time, and cracks in coating layer after storage at 40° C. under 75% RH

|  | Component | | | | | | | | | | | |
|---|---|---|---|---|---|---|---|---|---|---|---|---|
|  | Sodium lauryl sulfate | x | ○ | | | | | | | | | |
|  | L-HPC | ○ | x | | | | | | | | | |
|  | Microcrystalline cellulose | ○ | x | | | | | | | | | |
|  | Talc | ○ | x | | | | | | | | | |
|  | Crospovidone | x | x | | | | | | | | | |
|  | Maltitol | ○ | ○ | 20 | | | | | | | | 5 |
|  | Lactose | ○ | ○ | | | | | | | | 35 | 25 |
|  | Glycerin | ○ | ○ | | | | | | | | 5 | |
|  | Lactitol | ○ | ○ | 20 | 40 | 45 | | | | | | 10 |
|  | Trehalose | ○ | ○ | | | | 40 | | | | | |
|  | Mannitol | ○ | ○ | | | | | 40 | | | | |
|  | Maltose | ○ | ○ | | | | | | 40 | | | |
|  | Erythritol | | | | | | | | | 40 | | |
| Polymer | PVA | | | 30 | 30 | 20 | 30 | 30 | 30 | 30 | 30 | 30 |
|  | PVACOAT | | | | | | | | | | | |
|  | HPMC | | | | | | | | | | | |
| Lubricant | Silicone | | | | | | | | | | | |
|  | Polishing wax | | | | | 5 | | | | | | |
|  | Span80 | | | | | | | | | | | |
|  | Tween80 | | | | | | | | | | | |
|  | Liquid paraffin | | | | | | | | | | | |
| Light shading agent | Titanium oxide | | | 27 | 27 | 27 | 27 | 27 | 27 | 27 | 27 | 27 |
|  | Red ferric oxide | | | 3 | 3 | 3 | 3 | 3 | 3 | 3 | 3 | 3 |
| Evaluation | Oral disintegration time of coated tablet (sec) | | | 18 | 18 | 17 | 18 | 18 | 18 | 18 | 18 | 17 |
|  | Oral disintegration time of coating layer (sec) | | | 9 | 9 | 8 | 8 | 9 | 9 | 9 | 9 | 8 |
|  | Cracks after storage at 40° C. under 75% RH for one day | | | absent | absent | absent | absent | absent | absent | absent | absent | absent |
|  | The water-soluble substance of the present invention/ Polyvinyl alcohol resin | | | 1.33 | 1.33 | 2.25 | 1.33 | 1.33 | 1.33 | 1.33 | 1.33 | 1.33 |

|  | Component | Molecular weight of not more than 200 per a unit hydroxyl group | Water-soluble substance dissolving in an amount of 1 g or more in less than 10 mL of water at 20° C. | Ex. 19 | Ex. 20 | Ex. 21 | Ex. 22 | Ex. 23 | Ex. 24 | Ex. 25 | Ex. 26 |
|---|---|---|---|---|---|---|---|---|---|---|---|
| Additive | PEG6000 | x | ○ | | | | | | | | |
|  | Sodium lauryl sulfate | x | ○ | | | | | | | | |
|  | L-HPC | ○ | x | | | | | | | | |
|  | Microcrystalline cellulose | ○ | x | | | | | | | | |
|  | Talc | ○ | x | | | | | | | | |
|  | Crospovidone | x | x | | | | | | | | |
|  | Maltitol | ○ | ○ | 5 | | | | | | | |
|  | Lactose | ○ | ○ | 25 | 40 | 40 | 40 | 40 | 40 | 40 | 40 |
|  | Glycerin | ○ | ○ | | | | | | | | |
|  | Lactitol | ○ | ○ | | | | | | | | |
|  | Trehalose | ○ | ○ | | | | | | | | |
|  | Mannitol | ○ | ○ | | | | | | | | |
|  | Maltose | ○ | ○ | | | | | | | | |
|  | Erythritol | | | | | | | | | | |
| Polymer | PVA | | | 30 | 30 | 30 | 30 | 30 | 30 | 30 | 30 |
|  | PVACOAT | | | | | | | | | | |
|  | HPMC | | | | | | | | | | |
| Lubricant | Silicone | | | | | | | | | | |
|  | Polishing wax | | | | | | | | | | |
|  | Span80 | | | | | | | | | | |
|  | Tween80 | | | | | | | | | | |
|  | Liquid paraffin | | | | | | | | | | |
| Light shading agent | Titanium oxide | | | 27 | 27 | 27 | 27 | 27 | 27 | 27 | 27 |
|  | Red ferric oxide | | | 3 | 3 | 3 | 3 | 3 | 3 | 3 | 3 |
| Evaluation | Oral disintegration time of coated tablet (sec) | | | 31 | 18 | 22 | 28 | 22 | 35 | 26 | 18 |
|  | Oral disintegration time of coating layer (sec) | | | 4 | 9 | 3 | 4 | 3 | 12 | 5 | 7 |
|  | Cracks after storage at 40° C. under 75% RH for one day | | | absent | absent | absent | absent | absent | absent | absent | absent |
|  | The water-soluble substance of the present invention/ Polyvinyl alcohol resin | | | 1.33 | 1.33 | 1.33 | 1.33 | 1.33 | 1.33 | 1.33 | 1.33 |

Blending unit of formulation components is expressed in % by weight based on the weight of a coating layer.

TABLE 3

Light stabilizing effect

|  | Reference Example 1 | Example 7 |
|---|---|---|
| Percentage of residual drug (%) after irradiation with 2000 Lux/hr, total 600,000 Lux | 73.1% | 99.9% |

TABLE 4

Tablet hardness-enhancing effect

|  | Reference Example 1 | Example 7 |
|---|---|---|
| Tablet hardness | 37N | 52N |

TABLE 5

Friability-improving effect

|  | Amlodin (registered trademark) OD Tablets 2.5 mg | Example 19 |
|---|---|---|
| Friability (immediately after production) | 0.14% | 0.03% |
| Friability (after storage at 40° C. under 75% RH for two hours) | 0.54% | 0.06% |

As shown in Table 2, it was shown that a stable orally disintegrating coated tablet containing a drug, wherein the tablet is coated with a coating layer containing a water-soluble substance and a polyvinyl alcohol resin of not less than 5% by weight based on the weight of the coating layer, the water-soluble substance dissolving in an amount of 1 g or more in less than 10 mL of water at 20° C., having a hydroxyl group(s) in its molecule, and having a molecular weight of not more than 200 per a unit hydroxyl group, has excellent orally disintegrating properties compared to the formulations of Comparative Examples and at the same time does not cause a crack in the coating layer even when stored under high-humidity conditions of 40° C. and 75% RH. As shown in Table 3, it became apparent that a marked light stabilizing effect is shown and even in the case of a light-unstable drug, sufficient stability can be ensured when handling the medicament. Further, as shown in Table 4 and Table 5, the tablet hardness is enhanced and at the same time the friability is markedly improved, and these effects allow single-dose packaging of the orally disintegrating tablet which hitherto could not be packaged in a single-dose pack, which in turn improves drug compliance of patients and enhances therapeutic effects.

INDUSTRIAL APPLICABILITY

The present invention is applicable also to various drugs. Particularly, the light-unstable drug to which it has hitherto been difficult to apply can be made into an orally disintegrating tablet. In addition, the tablet hardness is enhanced and at the same time the friability is markedly improved, and these effects allow single-dose packaging of the orally disintegrating tablet which hitherto could not be packaged in a single-dose pack, which in turn improves drug compliance of patients and enhances therapeutic effects.

The invention claimed is:

1. A stable orally disintegrating coated tablet containing a drug, wherein said tablet is coated with a coating layer containing a water-soluble substance and a polyvinyl alcohol resin in an amount of 10 to 60% by weight based on the weight of said coating layer, wherein the weight ratio of said polyvinyl alcohol resin in said coating layer to said water-soluble substance is 1:0.2 to 1:6, and wherein said water-soluble substance is at least one of maltose, maltitol, sorbitol, xylitol, fructose, glucose, lactitol, isomaltose, lactose, erythritol, mannitol, trehalose, sucrose, and polyethylene glycol having an average molecular weight of not more than 400 and wherein said coating layer disintegrates in an oral cavity within 18 seconds and said orally disintegrating tablet disintegrates in an oral cavity within 60 seconds.

2. The stable orally disintegrating coated tablet according to claim 1, wherein said coating layer contains a light shading agent.

3. The stable orally disintegrating coated tablet according to claim 2, wherein said light shading agent is at least one of titanium oxide, red ferric oxide, yellow ferric oxide, black iron oxide, and kaolin.

4. The stable orally disintegrating coated tablet according to claim 2, wherein said light shading agent in said coating layer has a content of 0.1 to 40% by weight based on the weight of said coating layer.

5. The stable orally disintegrating coated tablet according to claim 1, wherein said drug is at least one of nalfurafine, amlodipine, donepezil, ebastine, selegiline, famotidine, irsogladine, brotizolam, olanzapine, lansoprazole, bepotastine, ramosetron, tamsulosin, naftopidil, polaprezinc, voglibose, rizatriptan, midodrine, risperidone, ondansetron, loratadine, montelukast, azulene sulfonate, etizolam, enalapril, captopril, glibenclamide, chlormadinone acetate, doxazosin, triazolam, domperidone, ketotifen, bromperidol, pravastatin, simvastatin, loperamide, lisinopril, rilmazafone, precipitated calcium carbonate, magnesium oxide, mecobalamin, alfacalcidol, bromocriptine, and pramipexole, and pharmaceutically acceptable salts and solvates thereof.

* * * * *

UNITED STATES PATENT AND TRADEMARK OFFICE
CERTIFICATE OF CORRECTION

| | | |
|---|---|---|
| PATENT NO. | : 8,715,730 B2 | Page 1 of 1 |
| APPLICATION NO. | : 13/257820 | |
| DATED | : May 6, 2014 | |
| INVENTOR(S) | : Takaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Eighteenth Day of August, 2015

Michelle K. Lee
*Director of the United States Patent and Trademark Office*